(12) United States Patent
Fishler et al.

(10) Patent No.: US 11,717,692 B2
(45) Date of Patent: Aug. 8, 2023

(54) PACEMAKER SYSTEMS AND METHODS USING MULTIPLE SENSORS FOR RATE RESPONSE PACING

(71) Applicant: PACESETTER, INC., Sylmar, CA (US)

(72) Inventors: Matthew G. Fishler, Scotts Valley, CA (US); Paul Paspa, Los Gatos, CA (US)

(73) Assignee: Pacesetter, Inc., Sylmar, CA (US)

( * ) Notice: Subject to any disclaimer, the term of this patent is extended or adjusted under 35 U.S.C. 154(b) by 468 days.

(21) Appl. No.: 16/510,793

(22) Filed: Jul. 12, 2019

(65) Prior Publication Data

US 2020/0054880 A1 Feb. 20, 2020

Related U.S. Application Data

(60) Provisional application No. 62/719,936, filed on Aug. 20, 2018.

(51) Int. Cl.
*A61N 1/378* (2006.01)
*A61N 1/365* (2006.01)
*A61N 1/375* (2006.01)

(52) U.S. Cl.
CPC ........... *A61N 1/378* (2013.01); *A61N 1/3655* (2013.01); *A61N 1/36542* (2013.01); *A61N 1/3756* (2013.01); *A61N 1/37512* (2017.08)

(58) Field of Classification Search
CPC .............. A61N 1/36542; A61N 1/3655; A61N 1/37512; A61N 1/3756; A61N 1/378
USPC ........................................ 607/1–95, 115–156
See application file for complete search history.

(56) References Cited

U.S. PATENT DOCUMENTS

| 4,803,987 A | 2/1989 | Calfee et al. |
| 4,905,697 A * | 3/1990 | Heggs ............... A61N 1/36585 607/18 |
| 6,096,061 A * | 8/2000 | Alt .................... A61N 1/36585 607/4 |
| 7,016,730 B2 | 3/2006 | Ternes |
| 7,937,148 B2 | 5/2011 | Jacobson |

(Continued)

FOREIGN PATENT DOCUMENTS

EP 0317986 A1 * 5/1989 ......... A61N 1/36585

OTHER PUBLICATIONS

Katritsis, et al. "New and Combined Sensors for Adaptive-Rate Pacing". Clin. Cardiol. 16, 240-248 (1993). 9 pages.

*Primary Examiner* — Jonathan T Kuo
*Assistant Examiner* — Vynn V Huh
(74) *Attorney, Agent, or Firm* — Vierra Magen Marcus LLP (57) ABSTRACT

Certain embodiments of the present technology disclosed herein relate to implantable systems, and methods for use therewith, that use a temperature sensor to initially detect an onset of patient activity, and then use a motion sensor to confirm or reject the initial detection of the onset of patient activity. Other embodiments of the present technology disclosed herein relate to implantable systems, and methods for use therewith, that use a motion sensor to initially detect an onset of patient activity, and then use a temperature sensor to confirm or reject the initial detection of the onset of patient activity. The use of both a motion sensor and a temperature sensor provides improvements over using just one of the types of sensors for rate responsive pacing.

20 Claims, 5 Drawing Sheets

(56) References Cited

U.S. PATENT DOCUMENTS

| | | |
|---|---|---|
| 8,543,204 B2 | 9/2013 | Ostroff |
| 8,543,205 B2 | 9/2013 | Ostroff |
| 9,440,081 B2 | 9/2016 | Demmer et al. |
| 9,814,887 B2 | 11/2017 | Nikolski et al. |
| 9,833,624 B2 | 12/2017 | Chin et al. |
| 2004/0098060 A1* | 5/2004 | Ternes ................. A61N 1/3708 607/17 |
| 2014/0031604 A1* | 1/2014 | Pless ..................... A61N 2/006 607/46 |
| 2014/0107723 A1* | 4/2014 | Hou ..................... A61N 1/3756 607/28 |

* cited by examiner

PACEMAKER SYSTEMS AND METHODS USING MULTIPLE SENSORS FOR RATE RESPONSE PACING

This application claims the benefit of U.S. Provisional Application No. 62/719,936, filed Aug. 20, 2018, and is incorporated herein by reference in its entirety to provide continuity of disclosure.

FIELD OF TECHNOLOGY

Embodiments described herein generally relate to methods and systems that perform rate responsive pacing.

BACKGROUND

The normal human heart supplies oxygen and removes waste products by providing a demand-based supply of blood to all tissues of the body. The volume of blood that is pumped through the body is determined by the person's heart rate and stroke volume. The heart beats approximately 60 bpm in a normal healthy resting individual and is regulated through a complex autonomic control mechanism which governs that the rate the sinoatrial (SA) node fires. It's the SA node that controls heart rate. As an individual does work, there is increased metabolic demand on tissues and the autonomic control system responds by causing the SA node to fire more rapidly, thereby increasing heart rate. In a healthy individual, interaction of the nervous system, SA node, and heart rate assures that a healthy balance is maintained throughout all levels of activity.

Most modern pacemakers have the ability to approximate the body's changing needs based on activity through the use of an electrical component called an accelerometer. For example, many pacemakers include an accelerometer that can detect motion (and more specifically, acceleration) as a proxy for activity. Changes in the motion as a person walks, runs, or does other activities send signals to the pacemaker's internal electronics to cause the pacemaker to increase heart rate to provide an active person with increased blood supply. A limitation of depending on an accelerometer to adjust pacing rate is that an accelerometer can interpret any motion as patient activity, such as riding in a car or on a bicycle down a bumpy road, which may result in a pacemaker inappropriately increasing a pacing rate. In other words, an accelerometer can mistakenly interpret certain increases in motion as increases in patient activity, even though such increases in motion are not actually due to increases in patient activity. Another limitation of depending on an accelerometer to adjust a pacing rate is that an accelerometer can, in certain instances, fail to detect increases in patient activity that are not accompanied by device vibration, such as when an individual rides a stationary bike while keeping their upper body relatively still. Either situation can cause a pacemaker to misinterpret activity and deliver inappropriate pacing rate control.

An alternative means of controlling the rate of a pacemaker is through the use of a blood temperature sensor. A rise in a person's core blood temperature (often first preceded by a small dip in the core blood temperature) is typically observed at the onset of activity and can be used as an alternative to an accelerometer. However, temperature changes alone may not always provide reliable feedback for all the possible scenarios that a patient may experience throughout the day. Changes in core blood temperature can also lag behind the start of activity, and thus, may not provide optimal cardiac response at activity onset, or can falsely signal activity if temperature changes are experienced without activity (e.g., in response to an individual going into a cool swimming pool on a hot day, or taking a hot shower, etc.).

SUMMARY

Certain embodiments of the present technology relate to an implantable system configured to be implanted in a patient, wherein the implantable system includes a temperature sensor, a motion sensor, a pulse generator, a controller, and a battery. The temperature sensor is configured to produce one or more outputs indicative of blood temperature when the temperature sensor is activated. The motion sensor is configured to produce one or more outputs indicative of motion when the motion sensor is activated. The pulse generator is configured to produce pulses that are used to pace a patient's heart. The controller is communicatively coupled to the temperature sensor, the motion sensor, and the pulse generator. The battery is configured to supply power to the controller and other components of the implantable system when they are activated.

In accordance with certain embodiments, the controller configured to initially detect an onset of patient activity based on at least one of the one or more outputs of the temperature sensor, and in response thereto, cause the pulse generator to increase the pacing rate from a base rate to an increased rate. The controller is also configured to selectively activate and use at least one of the one or more outputs of the motion sensor to confirm or reject an initial detection of an onset of patient activity, as detected based on at least one of the one or more outputs of the temperature sensor. Further, the controller is configured to cause the pulse generator to reduce the pacing rate from the increased rate to the base rate in response to the detection of the onset of patient activity being rejected using the at least one of the one or more outputs of the motion sensor. In accordance with certain embodiments, the motion sensor is kept in a low power mode when not selectively activated by the controller to use to confirm or reject the detection of the onset of patient activity, as initially detected based on at least one of the one or more outputs of the temperature sensor.

In accordance with certain embodiments, the controller is configured to initially detect an onset of patient activity, based on at least one of the one or more outputs of the temperature sensor, in response to detecting a change in blood temperature by at least a threshold amount of degrees within a threshold amount of time.

In accordance with certain embodiments, the controller is configured to cause the pulse generator to maintain the increased pacing rate, or further increase the pacing rate from the increased rate to a further increased rate, in response to the controller detecting continued patient activity based on at least one of the one or more outputs of the temperature sensor and/or based on at least one of the one or more outputs of the motion sensor.

In accordance with certain embodiments, the controller is configured to periodically activate the temperature sensor and to maintain the motion sensor in the low power mode until an initial detection of an onset of patient activity is detected based on at least one of the one or more outputs of the temperature sensor.

In accordance with certain embodiments, the implantable system is a leadless cardiac pacemaker that comprises a hermetic housing adapted and configured to be disposed in a chamber of a patient's heart. Each of the temperature sensor, the motion sensor, the pulse generator, the controller, and the battery is disposed in or part of the housing. The leadless cardiac pacemaker further comprises at least two electrodes supported by the housing and used to deliver pulses, produced by the pulse generator, to a patient's heart.

In accordance with other embodiments, the controller configured to initially detect an onset of patient activity based on at least one of the one or more outputs of the motion sensor, and in response thereto, cause the pulse generator to increase the pacing rate from a base rate to an increased rate. The controller is also configured to selectively activate and use at least one of the one or more outputs of the temperature sensor to confirm or reject an initial detection of an onset of patient activity, as detected based on at least one of the one or more outputs of the motion sensor. Further, the controller is configured to cause the pulse generator to reduce the pacing rate from the increased rate to the base rate in response to the detection of the onset of patient activity being rejected using the temperature sensor. In accordance with certain embodiments, the temperature sensor is kept in a low power mode when not selectively activated by the controller to confirm or reject the detection of the onset of patient activity, as initially detected based on at least one of the one or more outputs of the motion sensor.

In accordance with certain embodiments, the controller is configured to initially detect an onset of patient activity, based on at least one of the one or more outputs of the motion sensor, in response to detecting an increase in motion by at least a threshold amount for at least a threshold amount of time.

In accordance with certain embodiments, the controller is configured to cause the pulse generator to further increase the pacing rate from the increased rate to a further increased rate in response to the controller detecting continued patient activity based on at least one of the one or more outputs of the temperature sensor and/or based on at least one of the one or more outputs of the motion sensor.

In accordance with certain embodiments, the controller is configured to periodically activate the motion sensor and to maintain the temperature sensor in the low power mode until an initial detection of an onset of patient activity is detected based on at least one of the one or more outputs of the motion sensor.

Embodiments of the present technology also directed to related methods. For example, such a method can includes initially detecting an onset of patient activity based on at least one of the one or more outputs of the temperature sensor, and in response thereto, causing the pulse generator to increase the pacing rate from a base rate to an increased rate. The method further includes selectively activating the motion sensor and using at least one of the one or more outputs of the motion sensor to confirm or reject an initial detection of an onset of patient activity, as detected based on at least one of the one or more outputs of the temperature sensor. Further, the method includes causing the pulse generator to reduce the pacing rate from the increased rate to the base rate in response to the detection of the onset of patient activity being rejected using the at least one of the one or more outputs of the motion sensor. The method can also involve maintaining the motion sensor is in a low power mode when the motion sensor is not selectively activated to use to confirm or reject the detection of the onset of patient activity, as initially detected based on at least one of the one or more outputs of the temperature sensor.

Another method includes initially detecting an onset of patient activity based on at least one of the one or more outputs of the motion sensor, and in response thereto, causing the pulse generator to increase the pacing rate from a base rate to an increased rate. This method also includes selectively activating the temperature sensor and using at least one of the one or more outputs of the temperature sensor to confirm or reject an initial detection of an onset of patient activity, as detected based on at least one of the one or more outputs of the motion sensor. The method further includes causing the pulse generator to reduce the pacing rate from the increased rate to the base rate in response to the detection of the onset of patient activity being rejected using the at least one of the one or more outputs of the temperature sensor. The method can further include maintaining the temperature sensor is in a low power mode when the temperature sensor is not selectively activated to use to confirm or reject the detection of the onset of patient activity, as initially detected based on at least one of the one or more outputs of the motion sensor.

This summary is not intended to be a complete description of the embodiments of the present technology. Other features and advantages of the embodiments of the present technology will appear from the following description in which the preferred embodiments have been set forth in detail, in conjunction with the accompanying drawings and claims.

BRIEF DESCRIPTION OF THE DRAWINGS

Embodiments of the present technology relating to both structures and methods of operation may best be understood by referring to the following description and accompanying drawings, in which similar referenced characters denote similar elements throughout the several views.

DETAILED DESCRIPTION

Certain embodiments of the present technology relate to implantable systems, and methods for use therewith, that use a temperature sensor to initially detect an onset of patient activity, and then use a motion sensor to confirm or reject the initial detection of the onset of patient activity. Other embodiments of the present technology relate to implantable systems, and methods for use therewith, that use a motion sensor to initially detect an onset of patient activity, and then use a temperature sensor to confirm or reject the initial detection of the onset of patient activity.

Before providing addition details of the specific embodiments of the present technology mentioned above, an exemplary system in which embodiments of the present technology can be used will first be described with reference to FIGS. 1A, 1B and 2. More specifically, FIGS. 1A, 1B and 2 will be used to describe an exemplary cardiac pacing system, wherein pacing and sensing operations can be performed by multiple medical devices, which may include one or more leadless cardiac pacemakers, an implantable cardioverter-defibrillator (ICD), such as a subcutaneous-ICD, and/or a programmer reliably and safely coordinate pacing and/or sensing operations.

Figure 1A:
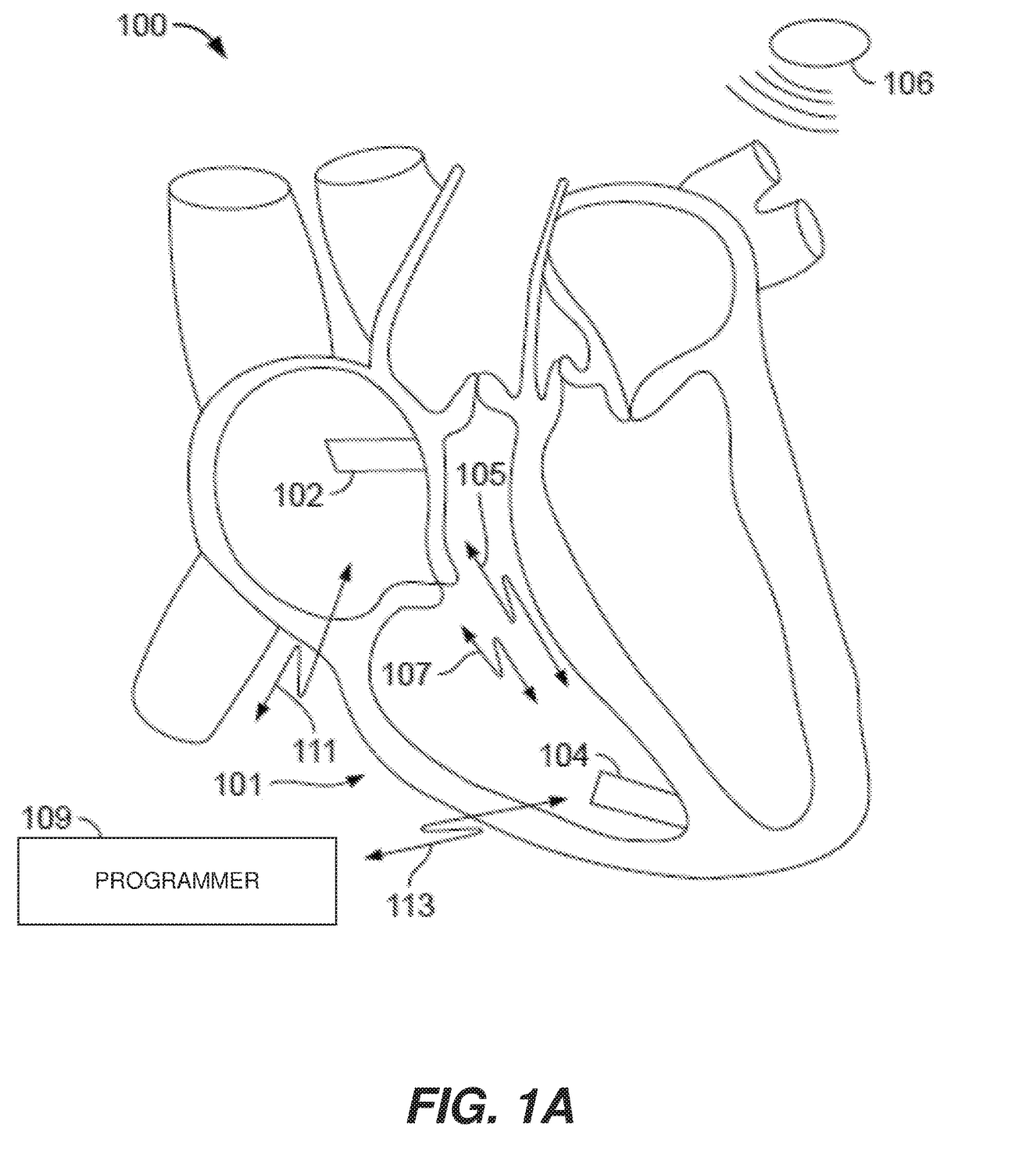
FIG. 1A illustrates a system formed in accordance with certain embodiments described herein as implanted in a heart.

FIG. 1A illustrates a system 100 that is configured to be implanted in a heart 101. The system 100 includes two or more leadless pacemakers (LPs) 102 and 104 located in different chambers of the heart. LP 102 is located in a right atrium, while LP 104 is located in a right ventricle. In FIG. 1A, LPs 102 and 104 may communicate with one another to inform one another of various local physiologic activities, such as local intrinsic events, local paced events and the like. LPs 102 and 104 may be constructed in a similar manner, but operate differently based upon which chamber LP 102 or 104 is located. It would also be possible for only one of the LPs 102 and 104 to be implanted in one chamber of the heart. However, for the remaining description of FIGS. 1 and 2 it will be assumed the both LPs 102 and 104 are implanted.

In certain embodiments, LPs 102 and 104 communicate with one another, and/or with an ICD 106, by conductive communication through the same electrodes that are used for sensing and/or delivery of pacing therapy. The LPs 102 and 104 may also be able to use conductive communications to communicate with an external device, e.g., a programmer 109, having electrodes placed on the skin of a patient within with the LPs 102 and 104 are implanted. While not shown (and not preferred, since it would increase the size of the LPs 102 and 104), the LPs 102 and 104 can potentially include an antenna and/or telemetry coil that would enable them to communicate with one another, the ICD 106 and/or an external device using RF or inductive communication.

In some embodiments, one or more LPs 102 and 104 can be co-implanted with the ICD 106. Each LP 102, 104 uses two or more electrodes located within, on, or within a few centimeters of the housing of the pacemaker, for pacing and sensing at the cardiac chamber, for bidirectional communication with one another, with the programmer 109, and the ICD 106.

While the methods, devices and systems described herein include examples primarily in the context of LPs, it is understood that the methods, devices and systems described herein may be utilized with various other types of implanted devices. By way of example, the methods, devices and systems may be or use other implantable medical devices (IMDs) implanted in a human, not just LPs.

Figure 1B:
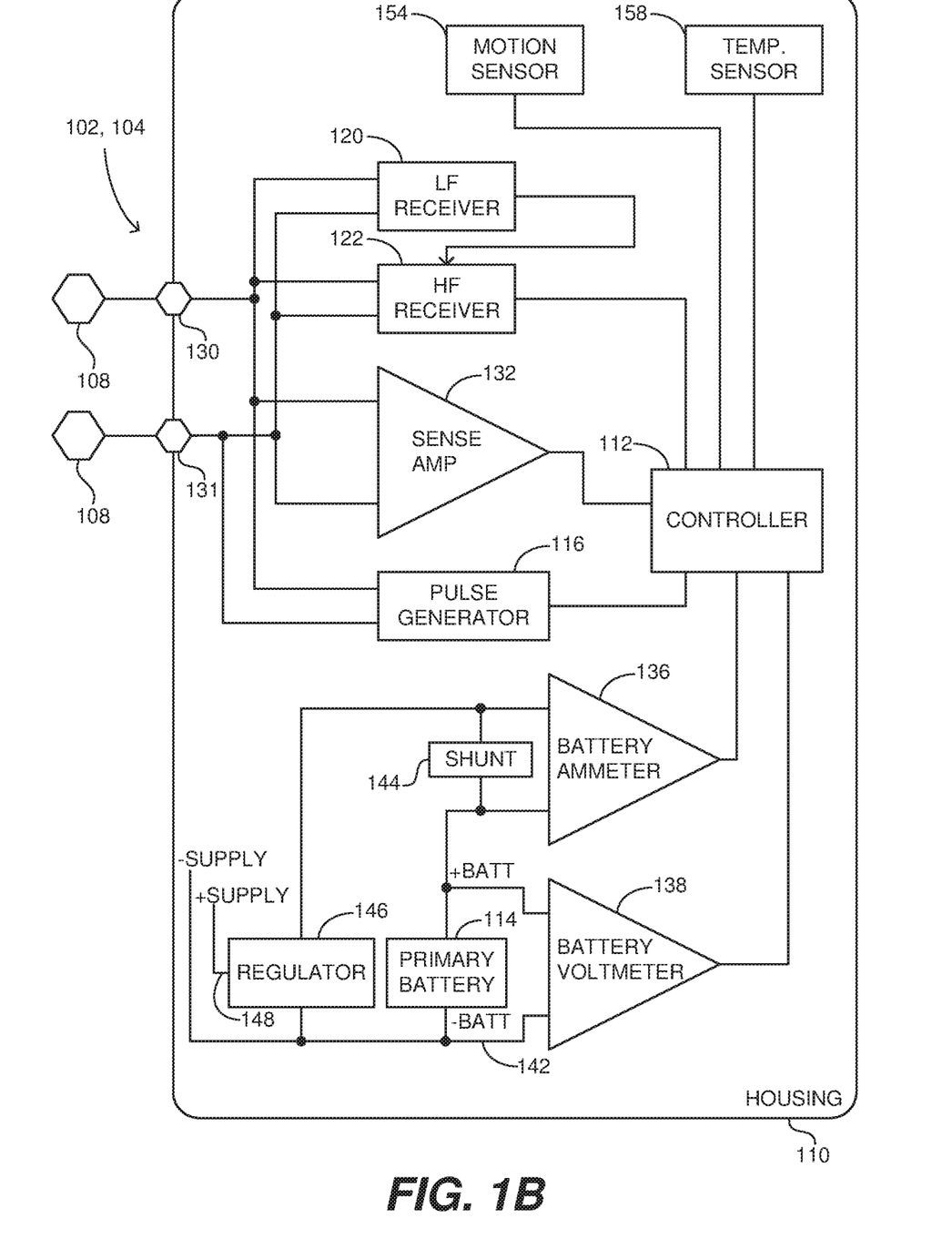
FIG. 1B is a block diagram of a single leadless pacemaker (LP) in accordance with certain embodiments herein.

Referring to FIG. 1B, a block diagram shows an embodiment for portions of the electronics within LPs 102 and 104. LP 102, 104 includes first and second receivers 120 and 122 that collectively define separate first and second communication channels 105 and 107 (FIG. 1A), (among other things) between LPs 102 and 104. Although first and second receivers 120 and 122 are depicted, in other embodiments, LP 102, 104 may only include first receiver 120, or may include additional receivers other than first and second receivers 120 and 122. As will be described in additional detail below, the pulse generator 116 can function as a transmitter that transmits implant-to-implant (121) communication signals using the electrodes 108. Usage of the electrodes 108 for communication enables the one or more LPs 102 and 104 to perform antenna-less and telemetry coil-less communication.

In accordance with certain embodiments, when one of the LPs 102 and 104 senses an intrinsic event or delivers a paced event, the corresponding LP 102, 104 transmits an implant event message to the other LP 102, 104. For example, when an atrial LP 102 senses/paces an atrial event, the atrial LP 102 transmits an implant event message including an event marker indicative of a nature of the event (e.g., intrinsic/sensed atrial event, paced atrial event). When a ventricular LP 104 senses/paces a ventricular event, the ventricular LP 104 transmits an implant event message including an event marker indicative of a nature of the event (e.g., intrinsic/sensed ventricular event, paced ventricular event). In certain embodiments, LP 102, 104 transmits an implant event message to the other LP 102, 104 preceding the actual pace pulse so that the remote LP can blank its sense inputs in anticipation of that remote pace pulse (to prevent inappropriate crosstalk sensing).

Still referring to FIG. 1B, each LP 102, 104 is shown as including a controller 112 and a pulse generator 116. The controller 112 can include, e.g., a microprocessor (or equivalent control circuitry), RAM and/or ROM memory, logic and timing circuitry, state machine circuitry, and I/O circuitry, but is not limited thereto. The controller 112 can further include, e.g., timing control circuitry to control the timing of the stimulation pulses (e.g., pacing rate, atrio-ventricular (AV) delay, atrial interconduction (A-A) delay, or ventricular interconduction (V-V) delay, etc.). Such timing control circuitry may also be used for the timing of refractory periods, blanking intervals, noise detection windows, evoked response windows, alert intervals, marker channel timing, and so on. The controller 112 can further include other dedicated circuitry and/or firmware/software components that assist in monitoring various conditions of the patient's heart and managing pacing therapies. The controller 112 and the pulse generator 116 may be configured to transmit event messages, via the electrodes 108, in a manner that does not inadvertently capture the heart in the chamber where LP 102, 104 is located, such as when the associated chamber is not in a refractory state. In addition, a LP 102, 104 that receives an event message may enter an "event refractory" state (or event blanking state) following receipt of the event message. The event refractory/blanking state may be set to extend for a determined period of time after receipt of an event message in order to avoid the receiving LP 102, 104 from inadvertently sensing another signal as an event message that might otherwise cause retriggering. For example, the receiving LP 102, 104 may detect a measurement pulse from another LP 102, 104 or programmer 109.

In accordance with certain embodiments herein, programmer 109 may communicate over a programmer-to-LP channel, with LP 102, 104 utilizing the same communication scheme. The external programmer 109 may listen to the event message transmitted between LP 102, 104 and synchronize programmer to implant communication such that programmer 109 does not transmit communication signals 113 until after an implant to implant messaging sequence is completed.

In accordance with certain embodiments, LP 102, 104 may combine transmit operations with therapy. The transmit event marker may be configured to have similar characteristics in amplitude and pulse-width to a pacing pulse and LP 102, 104 may use the energy in the event messages to help capture the heart. For example, a pacing pulse may normally be delivered with pacing parameters of 2.5V amplitude, 500 ohm impedance, 60 bpm pacing rate, 0.4 ms pulse-width. The foregoing pacing parameters correspond to a current draw of about 1.9 µA. The same LP 102, 104 may implement an event message utilizing event signaling parameters for amplitude, pulse-width, pulse rate, etc. that correspond to a current draw of approximately 0.5 µA for transmit.

LP 102, 104 may combine the event message transmissions with pacing pulses. For example, LP 102, 104 may use a 50 μs wakeup transmit pulse having an amplitude of 2.5V which would draw 250 nC (nano Coulombs) for an electrode load of 500 ohm. The pulses of the transmit event message may be followed by an event message encoded with a sequence of short duration pulses (for example 16, 2 μs on/off bits) which would draw an additional 80 nC. The event message pulse would then be followed by the remaining pulse-width needed to reach an equivalent charge of a nominal 0.4 ms pace pulse. In this case, the current necessary to transmit the marker is essentially free as it was used to achieve the necessary pace capture anyhow. With this method, the savings in transmit current could be budgeted for the receiver or would allow for additional longevity.

When LP 102 or 104 senses an intrinsic event, it can send a qualitatively similar event pulse sequence (but indicative of a sensed event) without adding the pace pulse remainder. As LP 102, 104 longevity calculations are designed based on the assumption that LP 102, 104 will deliver pacing therapy 100% of the time, transmitting an intrinsic event marker to another LP 102, 104 will not impact the nominal calculated LP longevity.

In some embodiments, the individual LP 102 can comprise a hermetic housing 110 configured for placement on or attachment to the inside or outside of a cardiac chamber and at least two leadless electrodes 108 proximal to the housing 110 and configured for bidirectional communication with at least one other device 106 within or outside the body.

Referring to FIG. 1B, the LP 102 (or 104) is shown as including a motion sensor 154 which is hermetically contained within the housing 110 and adapted to sense motion. FIG. 1B also shows that the LP 102 (or 104) includes a temperature sensor 158 adapted to sense core blood temperature. LP 102 and LP 104 can each include both their own motion sensor 154 and temperature sensor 158. It would also be possible for one of the LPs 102, 104 to include a motion sensor 154, and the other to include a temperature sensor 158, and that the LP that includes the motion sensor 154 transmit motion information to the other LP, and that the LP that includes the temperature sensor 158 transmit temperature information to the other LP. Other variations are also possible, e.g., if the system also includes the ICD 106, which can include a temperature sensor and/or a motion sensor.

The temperature sensor 158 can be any one of various different types of well known temperature sensors, or can be a future developed temperature sensor. For one example, the temperature sensor 158 can be a thermistor, which is a type of resistor whose resistance is dependent on temperature. Such a thermistor can be configured to sense the temperature of blood surrounding the LP through its housing 110. Exemplary details of such a thermistor are disclosed in U.S. Pat. No. 8,543,205, titled "Temperature Sensor for a Leadless Cardiac Pacemaker", and assigned on its face to Nanostim, Inc. located in Sunnyvale, Calif. The use of other types of temperature sensors are also possible and within the scope of the embodiments disclosed herein.

The one or more signals output by the temperature sensor 158 can be analyzed by the controller 112 and/or other circuitry. In certain embodiments, the temperature sensor 158 is packaged along with an integrated circuit (IC) that is designed to analyze the signal(s) in generates. In such embodiments, an output of the packaged sensor/IC can be an indication of temperature. In other embodiments, the temperature sensor 158 can be packaged along with an IC that performs signal conditioning (e.g., amplification and/or filtering), performs analog-to-digital conversions, and stores digital data (indicative of the sensor output) in memory (e.g., RAM, which may or may not be within the same package). In such embodiments, the controller 112 or other circuitry can read the digital data from the memory and analyze the digital data. Other variations are also possible, and within the scope of the present technology.

The motion sensor 154 can be any one of various different types of well known motion sensors, or can be a future developed motion sensor. For one example, the motion sensor 154 can be an accelerometer. Such an accelerometer can be or include, e.g., a MEMS (micro-electromechanical system) multi-axis accelerometer of the type exploiting capacitive or optical cantilever beam techniques, or a piezoelectric accelerometer that employs the piezoelectric effect of certain materials to measure dynamic changes in mechanical variables (e.g., acceleration, and/or vibration), but is not limited thereto, which can be used to detection motion of a patient in which the LP (or other IMD) Including the accelerometer is implanted. Where the accelerometer is a multi-axis accelerometer it can include two or three sensors aligned along orthogonal axes. Exemplary multi-axis accelerometers (also referred to as multi-dimensional accelerometers) that can be used are described in U.S. Pat. No. 6,658,292 (Kroll et al.) and U.S. Pat. No. 6,466,821 (Planca et al.), each of which is incorporated herein by reference. For another example, a commercially available micro-electromechanical system (MEMS) accelerometer marketed as the ADXL345 by Analog Devices, Inc. (headquartered in Norwood, Mass.) is a three-axis accelerometer and includes polysilicon springs that provide a resistance against acceleration forces. The term MEMS has been defined generally as a system or device having microcircuitry on a tiny silicon chip into which some mechanical device such as a mirror or a sensor has been manufactured. The aforementioned ADXL345 includes a micro-machined accelerometer co-packaged with a signal processing IC.

Another commercially available MEMS accelerometer is the ADXL327 by Analog Devices, Inc., which is a small, thin, low power, complete three axis accelerometer with signal conditioned voltage outputs. In the ADXL327, the mechanical sensor and signal conditioning IC are packaged together. A further commercially available MEMS accelerometer that can be used is the LIS3DH three-axis accelerometer by STMicroelectronics (headquartered in Geneva, Switzerland). Additional and/or alternative types of accelerometers may also be used. For example, it is also within the scope of the present technology for motion sensor 154 to be a beam-type of accelerometer, an example of which is described in U.S. Pat. No. 6,252,335 (Nilsson et al.), which is incorporated herein by reference.

In certain embodiments, the motion sensor 154 is implemented using one or more strain gauges. For example, a conventional type of strain gauge is formed of a thin film with a conductive wire or wires and associated terminals where tension causes an increase in resistance at the terminals and where compression decreases resistance at the terminals (e.g., a piezoresistive gauge). Vibrations and/or acoustics may cause such a film to cycle between tension and compression and hence produce an oscillating signal as resistance changes. The oscillating signal may be analyzed to determine the frequency of oscillation and/or the morphology of the signal. A strain gauge may be configured to sense strain along a particular direction. Multiple strain gauges may be included in the motion sensor 154 to sense strain along different directions.

One or more signals produced and output by the motion sensor 154 may be analyzed with respect to frequency content, energy, duration, amplitude and/or other characteristics. Such signals may or may not be amplified and/or filtered prior to being analyzed. For example, filtering may be performed using lowpass, highpass and/or bandpass filters. The signals output by the motion sensor 154 can be analog signals, which can be analyzed in the analog domain, or can be converted to digital signals (by an analog-to-digital converter) and analyzed in the digital domain. Alternatively, the signals output by the motion sensor 154 can already be in the digital domain.

The one or more signals output by the motion sensor 154 can be analyzed by the controller 112 and/or other circuitry. In certain embodiments, the motion sensor 154 is packaged along with an integrated circuit (IC) that is designed to analyze the signal(s) in generates. In such embodiments, an output of the packaged sensor/IC can be an indication of motion. In other embodiments, the motion sensor 154 can be packaged along with an IC that performs signal conditioning (e.g., amplification and/or filtering), performs analog-to-digital conversions, and stores digital data (indicative of the sensor output) in memory (e.g., RAM, which may or may not be within the same package). In such embodiments, the controller 112 or other circuitry can read the digital data from the memory and analyze the digital data. Other variations are also possible, and within the scope of the present technology.

FIG. 1B depicts a single LP 102 (or 104) and shows the LP's functional elements substantially enclosed in a hermetic housing 110. The LP 102 (or 104) has at least two electrodes 108 located within, on, or near the housing 110, for delivering pacing pulses to and sensing electrical activity from the muscle of the cardiac chamber, for sensing motion, for sensing temperature, and for bidirectional communication with at least one other device within or outside the body. Hermetic feedthroughs 130, 131 conduct electrode signals through the housing 110. The housing 110 contains a primary battery 114 to supply power for pacing, sensing, and communication. The housing 110 also contains circuits 132 for sensing cardiac activity from the electrodes 108, receivers 120, 122 for receiving information from at least one other device via the electrodes 108, and the pulse generator 116 for generating pacing pulses for delivery via the electrodes 108 and also for transmitting information to at least one other device via the electrodes 108. The housing 110 can further contain circuits for monitoring device health, for example a battery current monitor 136 and a battery voltage monitor 138, and can contain circuits for controlling operations in a predetermined manner.

The electrodes 108 can be configured to communicate bidirectionally among the multiple leadless cardiac pacemakers and/or the implanted ICD 106 to coordinate pacing pulse delivery and optionally other therapeutic or diagnostic features using messages that identify an event at an individual pacemaker originating the message and a pacemaker receiving the message react as directed by the message depending on the origin of the message. An LP 102, 104 that receives the event message reacts as directed by the event message depending on the message origin or location. In some embodiments or conditions, the two or more leadless electrodes 108 can be configured to communicate bidirectionally among the one or more leadless cardiac pacemakers 102 and/or the ICD 106 and transmit data including designated codes for events detected or created by an individual pacemaker. Individual pacemakers can be configured to issue a unique code corresponding to an event type and a location of the sending pacemaker.

In some embodiments, an individual LP 102, 104 can be configured to deliver a pacing pulse with an event message encoded therein, with a code assigned according to pacemaker location and configured to transmit a message to one or more other leadless cardiac pacemakers via the event message coded pacing pulse. The pacemaker or pacemakers receiving the message are adapted to respond to the message in a predetermined manner depending on type and location of the event.

Moreover, information communicated on the incoming channel can also include an event message from another leadless cardiac pacemaker signifying that the other leadless cardiac pacemaker has sensed a heartbeat or has delivered a pacing pulse, and identifies the location of the other pacemaker. For example, LP 104 may receive and relay an event message from LP 102 to the programmer. Similarly, information communicated on the outgoing channel can also include a message to another leadless cardiac pacemaker or pacemakers, or to the ICD, that the sending leadless cardiac pacemaker has sensed a heartbeat or has delivered a pacing pulse at the location of the sending pacemaker.

Referring again to FIGS. 1 and 2, the cardiac pacing system 100 may comprise an implantable cardioverter-defibrillator (ICD) 106 in addition to leadless cardiac pacemaker 102, 104 configured for implantation in electrical contact with a cardiac chamber and for performing cardiac rhythm management functions in combination with the implantable ICD 106. The implantable ICD 106 and the one or more leadless cardiac pacemakers 102, 104 configured for leadless intercommunication by information conduction through body tissue and/or wireless transmission between transmitters and receivers in accordance with the discussed herein. As mentioned above, the ICD 106 can include its own motion sensor and/or temperature sensor.

In a further embodiment, a cardiac pacing system 100 comprises at least one LP 102, 104 configured for implantation in electrical contact with a cardiac chamber and configured to perform cardiac pacing functions in combination with the co-implanted ICD 106. An LP 102, 104 comprise at least two leadless electrodes 108 configured for delivering cardiac pacing pulses, sensing evoked and/or natural cardiac electrical signals, and transmitting information to the co-implanted ICD 106.

As shown in the illustrative embodiments, an LP 102, 104 can comprise two or more leadless electrodes 108 configured for delivering cardiac pacing pulses, sensing evoked and/or natural cardiac electrical signals, and bidirectionally communicating with the co-implanted ICD 106.

LP 102, 104 can be configured for operation in a particular location and a particular functionality at manufacture and/or at programming by an external programmer 109. Bidirectional communication among the multiple leadless cardiac pacemakers can be arranged to communicate notification of a sensed heartbeat or delivered pacing pulse event and encoding type and location of the event to another implanted pacemaker or pacemakers. LP 102, 104 receiving the communication decode the information and respond depending on location of the receiving pacemaker and predetermined system functionality.

In some embodiments, the LPs 102 and 104 are configured to be implantable in any chamber of the heart, namely either atrium (RA, LA) or either ventricle (RV, LV). Furthermore, for dual-chamber configurations, multiple LPs may be co-implanted (e.g., one in the RA and one in the RV, one in the RV and one in the coronary sinus proximate the LV). Certain pacemaker parameters and functions depend on (or assume) knowledge of the chamber in which the pacemaker is implanted (and thus with which the LP is interacting; e.g., pacing and/or sensing). Some non-limiting examples include: sensing sensitivity, an evoked response algorithm, use of AF suppression in a local chamber, blanking and refractory periods, etc. Accordingly, each LP preferably knows an identity of the chamber in which the LP is implanted, and processes may be implemented to automatically identify a local chamber associated with each LP.

Processes for chamber identification may also be applied to subcutaneous pacemakers, ICDs, with leads and the like. A device with one or more implanted leads, identification and/or confirmation of the chamber into which the lead was implanted could be useful in several pertinent scenarios. For example, for a DR or CRT device, automatic identification and confirmation could mitigate against the possibility of the clinician inadvertently placing the V lead into the A port of the implantable medical device, and vice-versa. As another example, for an SR device, automatic identification of implanted chamber could enable the device and/or programmer to select and present the proper subset of pacing modes (e.g., AAI or VVI), and for the IPG to utilize the proper set of settings and algorithms (e.g., V-AutoCapture vs. ACap-Confirm, sensing sensitivities, etc.).

Also shown in FIG. 1B, the primary battery 114 has positive terminal 140 and negative terminal 142. Current from the positive terminal 140 of primary battery 114 flows through a shunt 144 to a regulator circuit 146 to create a positive voltage supply 148 suitable for powering the remaining circuitry of the pacemaker 102. The shunt 144 enables the battery current monitor 136 to provide the controller 112 with an indication of battery current drain and indirectly of device health. The illustrative power supply can be a primary battery 114.

In various embodiments, LP 102, 104 can manage power consumption to draw limited power from the battery, thereby reducing device volume. Each circuit in the system can be designed to avoid large peak currents. For example, cardiac pacing can be achieved by discharging a tank capacitor (not shown) across the pacing electrodes. Recharging of the tank capacitor is typically controlled by a charge pump circuit. In a particular embodiment, the charge pump circuit is throttled to recharge the tank capacitor at constant power from the battery.

In some embodiments, the controller 112 in one leadless cardiac pacemaker 102 can access signals on the electrodes 108 and can examine output pulse duration from another pacemaker for usage as a signature for determining triggering information validity and, for a signature arriving within predetermined limits, activating delivery of a pacing pulse following a predetermined delay of zero or more milliseconds. The predetermined delay can be preset at manufacture, programmed via an external programmer, or determined by adaptive monitoring to facilitate recognition of the triggering signal and discriminating the triggering signal from noise. In some embodiments or in some conditions, the controller 112 can examine output pulse waveform from another leadless cardiac pacemaker for usage as a signature for determining triggering information validity and, for a signature arriving within predetermined limits, activating delivery of a pacing pulse following a predetermined delay of zero or more milliseconds.

Figure 2:
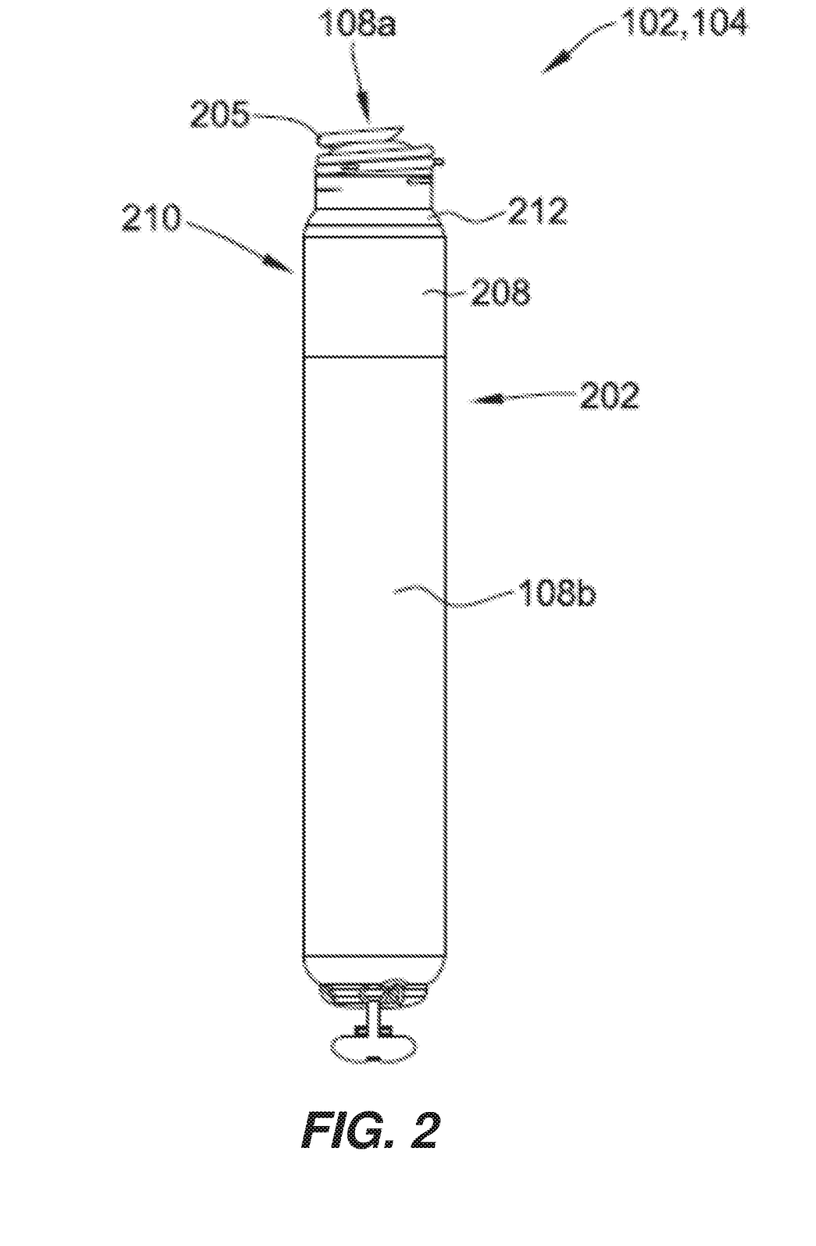
FIG. 2 illustrates an LP in accordance with certain embodiments herein.

FIG. 2 shows an LP 102, 104. The LP can include a hermetic housing 202 with electrodes 108a and 108b disposed thereon. As shown, electrode 108a can be separated from but surrounded partially by a fixation mechanism 205, and the electrode 108b can be disposed on the housing 202. The fixation mechanism 205 can be a fixation helix, a plurality of hooks, barbs, or other attaching features configured to attach the pacemaker to tissue, such as heart tissue. The electrodes 108a and 108b are examples of the electrodes 108 shown in and discussed above with reference to FIG. B.

The housing 202 can also include an electronics compartment 210 within the housing that contains the electronic components necessary for operation of the pacemaker, including, e.g., a pulse generator, receiver, a battery, and a processor for operation. The hermetic housing 202 can be adapted to be implanted on or in a human heart, and can be cylindrically shaped, rectangular, spherical, or any other appropriate shapes, for example.

The housing 202 can comprise a conductive, biocompatible, inert, and anodically safe material such as titanium, 316L stainless steel, or other similar materials. The housing 202 can further comprise an insulator disposed on the conductive material to separate electrodes 108a and 108b. The insulator can be an insulative coating on a portion of the housing between the electrodes, and can comprise materials such as silicone, polyurethane, parylene, or another biocompatible electrical insulator commonly used for implantable medical devices. In the embodiment of FIG. 2, a single insulator 208 is disposed along the portion of the housing between electrodes 108a and 108b. In some embodiments, the housing itself can comprise an insulator instead of a conductor, such as an alumina ceramic or other similar materials, and the electrodes can be disposed upon the housing.

As shown in FIG. 2, the pacemaker can further include a header assembly 212 to isolate 108a and 108b. The header assembly 212 can be made from PEEK, tecothane or another biocompatible plastic, and can contain a ceramic to metal feedthrough, a glass to metal feedthrough, or other appropriate feedthrough insulator as known in the art.

The electrodes 108a and 108b can comprise pace/sense electrodes, or return electrodes. A low-polarizatiop coating can be applied to the electrodes, such as sintered platinum, platinum-iridium, iridium, iridium-oxide, titanium-nitride, carbon, or other materials commonly used to reduce polarization effects, for example. In FIG. 2, electrode 108a can be a pace/sense electrode and electrode 108b can be a return electrode. The electrode 108b can be a portion of the conductive housing 202 that does not include an insulator 208.

Several techniques and structures can be used for attaching the housing 202 to the interior or exterior wall of the heart. A helical fixation mechanism 205, can enable insertion of the device endocardially or epicardially through a guiding catheter. A torqueable catheter can be used to rotate the housing and force the fixation device into heart tissue, thus affixing the fixation device (and also the electrode 108a in FIG. 2) into contact with stimulable tissue. Electrode 108b can serve as an indifferent electrode for sensing and pacing. The fixation mechanism may be coated partially or in full for electrical insulation, and a steroid-eluting matrix may be included on or near the device to minimize fibrotic reaction, as is known in conventional pacing electrode-leads.

Use of Motion and Temperature Sensors

As noted above, in the Background, most modern pacemakers have the ability to approximate the body's changing needs based on activity through the use of an electrical component called an accelerometer. For example, many pacemakers include an accelerometer that can detect motion and convert motion into tiny electrical impulses that can be detected as a proxy for activity. Changes in the motion as a person walks, runs, or does other activities send signals to the pacemaker's internal electronics to cause the pacemaker to increase heart rate to provide an active person with increased blood supply. A limitation of depending on an accelerometer to adjust pacing rate is that an accelerometer can interpret any motion as patient activity, such as riding in a car or on a bicycle down a bumpy road, which may result in a pacemaker inappropriately increasing a pacing rate. In other words, an accelerometer can mistakenly interpret certain increases in motion as increases in patient activity, even though such increases in motion are not actually due to increases in patient activity. Another limitation of depending on an accelerometer to adjust a pacing rate is that an accelerometer can, in certain instances, fail to detect increases in patient activity that are not accompanied by device vibration, such as when an individual rides a stationary bike while keeping their upper body relatively still. Either situation can cause a pacemaker to misinterpret activity and deliver inappropriate pacing rate control.

As also noted above, in the Background, an alternative potential means of controlling the rate of a pacemaker is through the use of a blood temperature sensor. A rise in a person's core blood temperature (often first preceded by a small dip in that core blood temperature) is typically observed at the onset of activity and can be used as an alternative to an accelerometer. However, temperature changes alone may not always provide reliable feedback for all the possible scenarios that a patient may experience throughout the day. Changes in core blood temperature can also lag behind the start of activity, and thus, may not provide optimal cardiac response at activity onset, or can falsely signal activity if temperature changes are experienced without activity (e.g., in response to an individual going into a cool swimming pool on a hot day, or taking a hot shower, etc.).

Embodiments of the present technology described herein relate to implantable systems, and methods for use therewith, that utilize both a motion sensor and a temperature sensor to improve rate adaptive pacing. Certain such embodiments, summarized with reference to FIG. 3, use a temperature sensor to initially detect an onset of patient activity, and then use a motion sensor to confirm or reject the initial detection of the onset of patient activity. Other embodiments, summarized with reference to FIG. 4, use a motion sensor to initially detect an onset of patient activity, and then use a temperature sensor to confirm or reject the initial detection of the onset of patient activity. Beneficially, both embodiments utilize a combination of motion and temperature sensors in an energy efficient manner. Both embodiments are for use with an implantable system configured to be implanted in a patient, wherein the system includes an implantable temperature sensor, an implantable motion sensor, an implantable pulse generator, a battery, and a controller communicatively coupled to the temperature sensor, the motion sensor, and the pulse generator. The implantable system can be or include a leadless pacemaker, such as the LP 102 and/or the LP 104, described above. The temperature sensor, e.g., 158 in FIG. 1B, can be configured to produce one or more outputs indicative of blood temperature when the temperature sensor is activated. The motion sensor, e.g., 154 in FIG. 1B, can be configured to produced one or more outputs indicative of motion when the motion sensor is activated. The pulse generator, e.g., 116 in FIG. 1B, can be configured to produce pulses that are used to pace a patient's heart. The controller, e.g., 112 in FIG. 1B, can receive, process and/or interpret outputs (e.g., digital or analog signals) received from the temperature sensor and/or the motion sensor. The controller can also control when the temperature sensor and/or motion sensor is/are activated, as well as when the temperature sensor and/or motion sensor is/are put in a low power mode to conserve power. The battery, e.g., 114 in FIG. 1B, can supply power to the controller, the pulse generator, and one or more other component(s) of the implantable system when the component(s) is/are activated.

Figure 3:
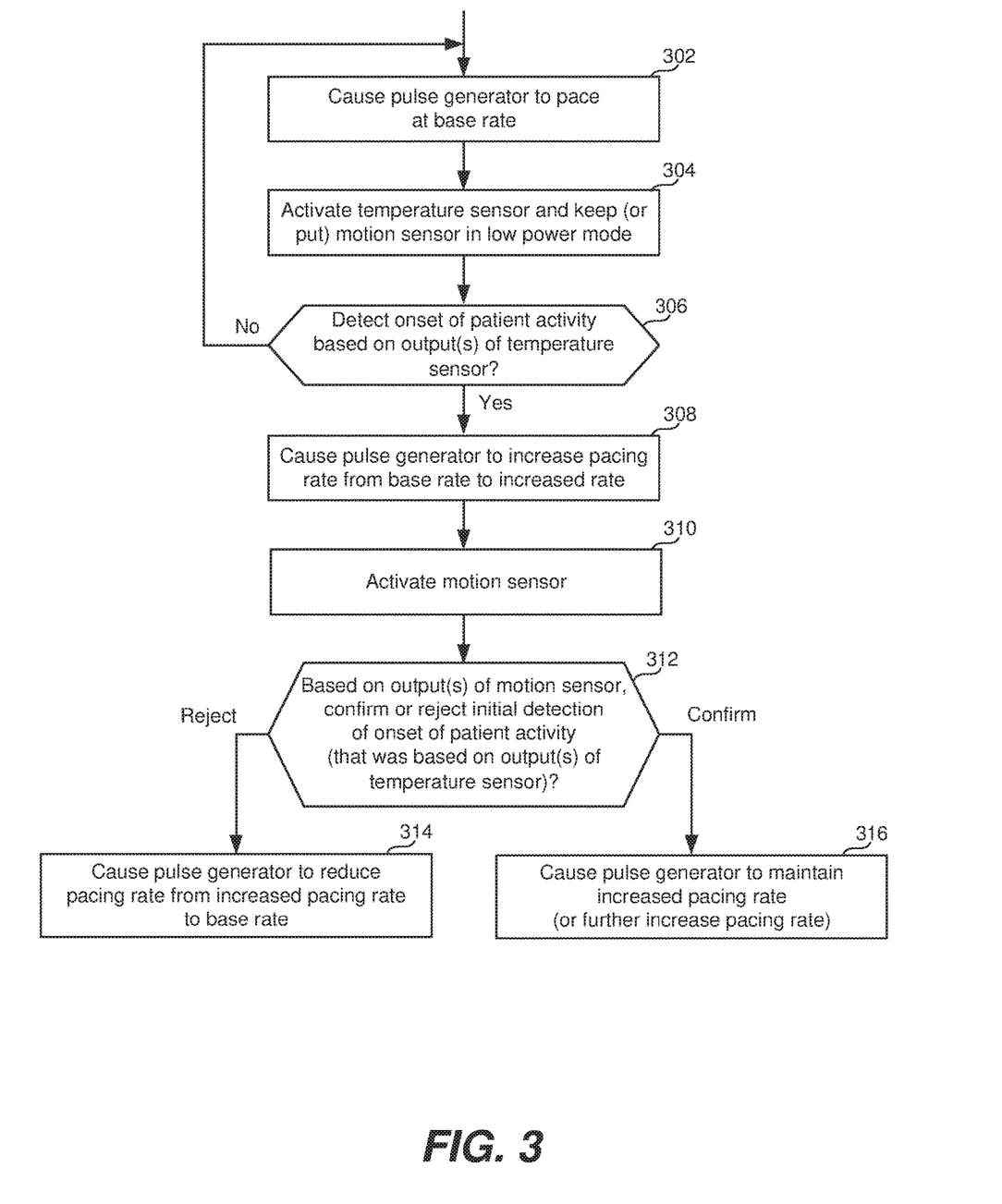
FIG. 3 is a high level flow diagram used to summarize certain embodiments of the present technology that use a temperature sensor to initially detect an onset of patient activity, and then use a motion sensor to confirm or reject the initial detection of the onset of patient activity.

Referring to high level flow diagram of FIG. 3, step 302 involves causing a pulse generator (e.g., 116) to pace at a base rate. Such a base rate can be, e.g., the resting pacing rate at which a patient is paced when they are at rest or otherwise not active. In certain embodiments the base rate is programmed by a physician or clinician for the specific patient, either before the system has been implanted, or after the system has been implanted. For example, a programmer (e.g., 109) can be used to program the base rate after the system has been implanted. Alternatively a default base rate can be programmed into in implantable system and used. Step 302 can be performed by a controller (e.g., 112) that is configured to control the frequency or rate of the pulses generated by the pulse generator (e.g., 116).

Still referring to FIG. 3, steps 304 involves activating the temperature sensor (e.g., 158) of the implantable system and keeping (or putting) the motion sensor (e.g., 154) of the implantable system in a low power mode. The low power mode can be, e.g., an inactive, disabled and/or sleep mode, during which time the motion sensor does not produce any output signals based upon which motion of the patient can be detected. Beneficially, when the motion sensor is in its low power mode it draws substantially no current from the battery (e.g., 114), and thus, reduces power consumption compared to if the motion sensor were activated. In FIG. 3, step 304 is shown after step 302, but these steps can alternatively be performed in reverse order or at the same time, but are not limited thereto.

Step 306 involves determining whether the onset of patient activity is detected based on at least one of one or more outputs of the temperature sensor (e.g., 158). For example, an output of the temperature sensor, which is indicative of sensed core blood temperature, can be monitored to determine whether the patient's core blood temperature has changed by at least a specified threshold amount within a specified threshold amount of time. Such an output of the temperature sensor can specify the patient's core blood temperature in degrees Celsius (C) or Fahrenheit (F), or can more generally be proportional to the patient's blood temperature, such that increases in the output are indicative of and proportional to increases in the patient's core blood temperature, and decreases in the output are indicative of and proportional to decreases in the patient's core blood temperature.

When a person changes from an inactive or resting state to an active state, the person's core blood temperature will often initially drop from a baseline or first core blood temperature to a second core blood temperature. In other words, initially there is often a small dip in the person's core blood temperature. This small dip in the person's core blood temperature is caused by vasodilation at an onset or anticipation of exercise or other activity. This initial drop in the core blood temperature is typically followed by a rise in the core blood temperature, or by a brief leveling off period followed by a rise in the core blood temperature. If the activity is brief the core blood temperature will typically slowly return to its baseline core blood temperature. However, if the activity or exercise continues, the core blood temperature will rise past the baseline core blood temperature to an elevated core blood temperature that will typically continue to rise until a maximum is reached or the activity ceases. After the activity ceases, the core blood temperature will typically slowly return to the baseline core blood temperature.

In accordance with certain embodiments, the onset of patient activity can be detected in response to detecting a drop in blood temperature by at least a threshold drop amount within a first specified amount of time. Additionally, or alternatively, the onset of patient activity can be detected in response to detecting an increase in blood temperature by a threshold increase amount within a second specified amount of time, which can be the same or different than the first specified amount of time. For example, the first specified amount of time can be 5 seconds, and the second specified amount of time can be 10 seconds, or vice versa, which examples are not intended to be limiting. The threshold drop amount can be, e.g., in the range of 0.03 to 0.24 degrees C., and in one embodiment can be 0.06 degrees C., but is not limited thereto. The threshold increase amount can be, e.g., in the range of 0.03 to 0.24 degrees C., and in one embodiment can be 0.12 degrees C., but is not limited thereto.

As shown in FIG. 3, if an onset of patient activity is not detected at step 306 (i.e., if the answer to the determination at step 306 is No), then flow returns to step 302. However, if the onset of patient activity is detected at step 306 (i.e., if the answer to the determination at step 306 is Yes), the flow goes to step 308.

Step 308, which is performed in response to the onset of patient activity being detected, involves causing the pulse generator (e.g., 116) to pace at an increased pacing rate that is greater than the base rate. Step 308 can be performed by a controller (e.g., 112) that is configured to control the frequency or rate of the pulses generated by the pulse generator (e.g., 116).

Step 310, which is also performed in response to the onset of patient activity being detected, involves activating the motion sensor (e.g., 154). Step 308 can be performed by the controller (e.g., 112). In FIG. 3, step 310 is shown after step 308, but these steps can alternatively be performed in reverse order or at the same time, but are not limited thereto.

Step 312 involves determining whether the onset of patient activity, as initially detected (at step 306) based on at least one of one or more outputs of the temperature sensor, is confirmed or rejected based on at least one of the one or more outputs of the motion sensor (e.g., 154). Assuming, for example, that the motion sensor is a one-axis accelerometer that produces one output indicative of motion, and more specifically acceleration, that one output can be compared to a threshold, and if the threshold is reached or exceeded then the onset of patient activity can be confirmed. Conversely, if the threshold is not reached or exceeded, then the initial detection of the onset of patient activity can be rejected. If the initial detection of the onset of patient activity is rejected, then flow goes to step 314. Step 314 involves causing the pulse generator (e.g., 116) to reduce the pacing rate from the increased rate back to the base rate. If the initial detection of the onset of patient activity is confirmed, then flow goes to step 316 and the pulse generator is controlled to maintain the increased pacing rate. Alternatively, at step 316, or a further step, the pacing rate can be further increased if the activity is maintained for at least some length of time, and/or if a level of the activity is increased further as detected using the temperature sensor and/or the motion sensor. Steps 312, 314 and/or 316 can be performed by a controller (e.g., 112). Such a controller (e.g., 112) can include one or more processors. Such a controller can additionally, or alternatively, including one or more comparators and/or logic gates that are collectively configured to compare one or more outputs to one or more respective thresholds and trigger responses in the manners summarized with reference to the high-level flow diagram of FIG. 3.

Assuming, for another example, that the motion sensor is a three-axis accelerometer that produces three outputs each indicative of motion (and more specifically acceleration) along a different one of three orthogonal axes, each of the three outputs can be compared to a respective threshold, which thresholds can be the same or different than one another. In one embodiment, at step 312 if any of the three outputs reaches or exceeds its respective threshold then the initial detection of the onset of patient activity (as initially detected at step 306) is confirmed, and otherwise is rejected. In another embodiment, at step 312 if at least two of the three outputs of the three-axis accelerometer reaches or exceeds its respective threshold then the initial detection of the onset of patient activity (as initially detected at step 306) is confirmed, and otherwise is rejected. In still another embodiment, at step 312 if all three outputs of the three-axis accelerometer reach or exceed its respective threshold then the initial detection of the onset of patient activity (as initially detected at step 306) is confirmed, and otherwise is rejected. Other variations are also possible and within the scope of the embodiments described herein.

Following step 314 flow can return to step 302. Following step 316 the pacing rate used to pace the patient's heart can be modulated (i.e., adjusted) based on the amount of activity detected, and then eventually, after the activity is finished the pacing rate can be returned to its base rate, at which point flow can return to step 302.

In accordance with certain embodiments, the temperature sensor (e.g., 158) can be continually activated and used to detect an initial onset of patient activity. To further conserve power, the temperature sensor can instead be periodically activated, e.g., once per minute or other length of time, and used to detect an initial onset of patient activity. In other words, the activating of the temperature sensor at step 304 can only be performed from time to time (e.g., periodically, or on a schedule) or alternatively can be continually performed, depending upon implementation.

In accordance with certain embodiments, the motion sensor is kept in the low power mode when the motion sensor is not selectively activated to be used to confirm or reject the detection of the onset of patient activity, as initially detected based on at least one of the one or more outputs of the temperature sensor.

In accordance with certain embodiments, the implantable system can differentiate physical non-cardiac motion from cardiac movement. For example, software, firmware and/or hardware can be used to subtract a baseline cardiac motion signal from accelerator motion data to discriminate non-cardiac physical motion from cardiac motion (also referred to as cardia movement). Such a baseline cardiac motion signal can be sensed using the motion sensor when it is known that the patient is not moving, e.g., while the patient is in a clinician or physician's office. Alternatively, or additionally, output(s) of the motion sensor can be ignored (e.g., blanked) during periods of cardiac motion, such as during periods of time between a QRS complex and a following T-wave, for example. Other variations are also possible and within the scope of the embodiments described herein.

In the embodiments described with reference to FIG. 3, the temperature sensor is used to initially detect the onset of patient activity, and then the motion sensor is activated and used to confirm or reject this initial detection. In the embodiments described with reference to FIG. 3, the base pacing rate is increased in response to temperature sensor being used to initially detect the onset of patient activity, to provide for a fast pacing rate adjustment. In an alternative embodiment, the base pacing rate is only increased following both the initial detection of the onset of patient activity using the temperature sensor, and the confirmation of the onset of patient activity as determined using the motion sensor. While this latter embodiment would conserve power, the power conservation occurs at the expense of a slower pacing rate adjustment.

In the embodiments described below with reference to FIG. 4, the motion sensor (e.g., 154) is used to initially detect the onset of patient activity, and then the temperature sensor (e.g., 158) is used to confirm or reject this initial detection.

Figure 4:
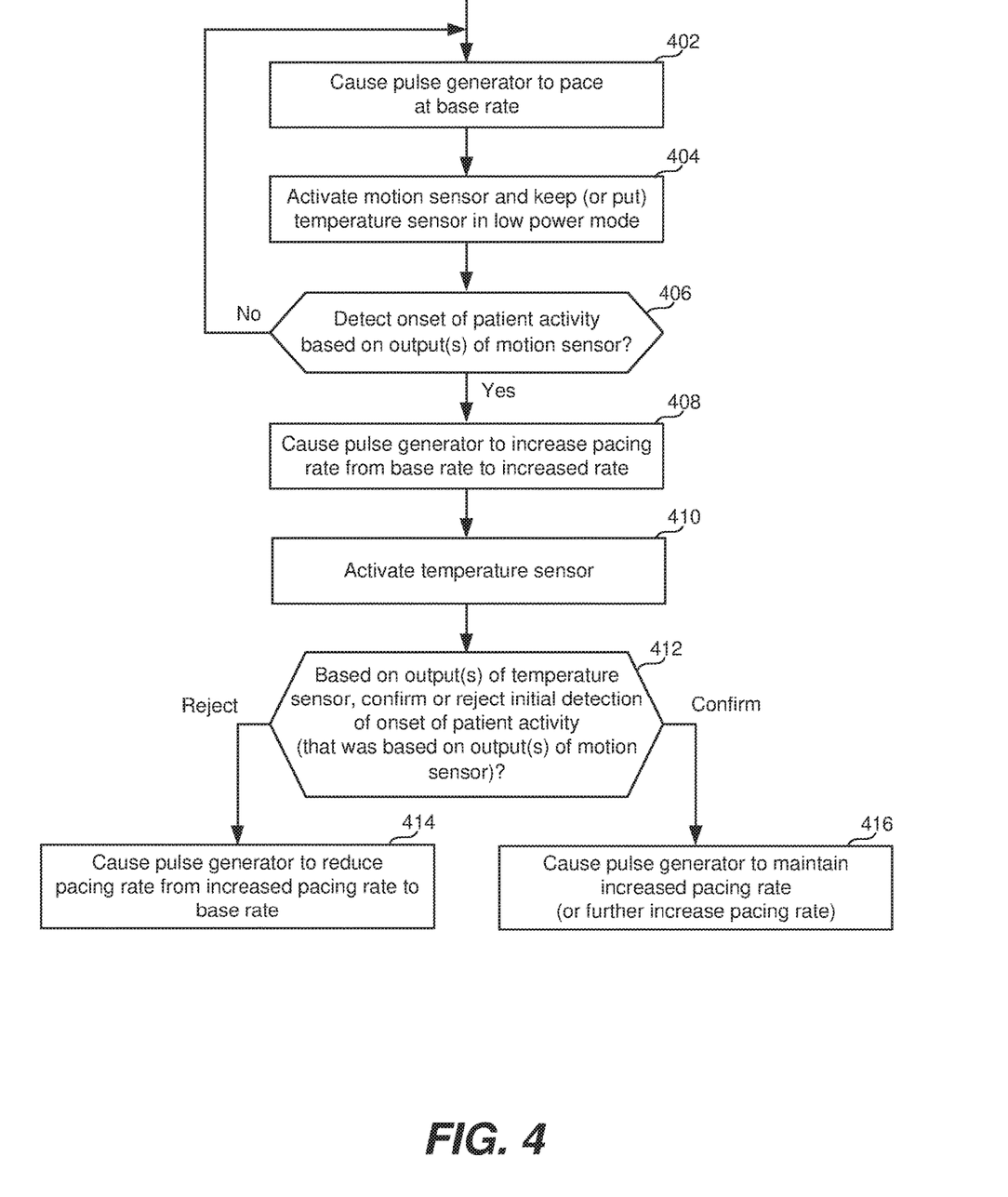
FIG. 4 is a high level flow diagram used to summarize certain embodiments of the present technology that use a motion sensor to initially detect an onset of patient activity, and then use a temperature sensor to confirm or reject the initial detection of the onset of patient activity.

Referring to high level flow diagram of FIG. 4, step 402 involves causing a pulse generator (e.g., 116) to pace at a base rate. Such a base rate can be, e.g., the resting pacing rate at which a patient is paced when they are at rest or otherwise not active. In certain embodiments the base rate is programmed by a physician or clinician for the specific patient, either before the system has been implanted, or after the system has been implanted. For example, a programmer (e.g., 109) can be used to program the base rate after the system has been implanted. Alternatively a default base rate can be programmed into in implantable system and used. Step 402 can be performed by a controller (e.g., 112) that is configured to control the frequency or rate of the pulses generated by the pulse generator (e.g., 116).

Still referring to FIG. 4, steps 404 involves activating the motion sensor (e.g., 154) of the implantable system and keeping (or putting) the temperature sensor (e.g., 158) of the implantable system in a low power mode. The low power mode can be, e.g., an inactive, disabled and/or sleep mode, during which time the temperature sensor does not produce any output signals based upon which core blood temperature of the patient can be detected. Beneficially, when the temperature sensor is in its low power mode it draws substantially no current from the battery (e.g., 114), and thus, reduces power consumption compared to if the temperature sensor were activated. In FIG. 4, step 404 is shown after step 402, but these steps can alternatively be performed in reverse order or at the same time, but are not limited thereto.

Step 406 involves determining whether the onset of patient activity is detected based on at least one of one or more outputs of the motion sensor. Assuming, for example, that the motion sensor is a one-axis accelerometer that produces one output indicative of motion, and more specifically acceleration, that one output can be compared to a threshold, and if the threshold is reached or exceeded then the onset of patient activity can be detected at step 406. Conversely, if the threshold is need reached or exceeded, then the onset of patient activity is not detected, and flow returns to step 402.

Assuming, for another example, that the motion sensor is a three-axis accelerometer that produces three outputs each indicative of motion (and more specifically acceleration) along a different one of three orthogonal axes, each of the three outputs can be compared to a respective threshold, which thresholds can be the same or different than one another. In one embodiment, at step 406 if any of the three outputs reaches or exceeds its respective threshold then the initial onset of patient activity is detected at step 406, and otherwise is not initially detected. In another embodiment, at step 406 if at least two of the three outputs of the three-axis accelerometer reaches or exceeds its respective threshold then the onset of patient activity is initially detected at step 406, and otherwise is not initially detected. In still another embodiment, at step 406 if all three outputs of the three-axis accelerometer reach or exceed its respective threshold then there is an initial detection of the onset of patient activity, and otherwise is not initially detected. Other variations are also possible and within the scope of the embodiments described herein.

As shown in FIG. 4, if an onset of patient activity is not detected at step 406 (i.e., if the answer to the determination at step 406 is No), then flow returns to step 402. However, if the onset of patient activity is detected at step 406 (i.e., if the answer to the determination at step 406 is Yes), the flow goes to step 408.

Step 408, which is performed in response to the onset of patient activity being detected, involves causing the pulse generator (e.g., 116) to pace at an increased pacing rate that is greater than the base rate. Step 408 can be performed by a controller (e.g., 112) that is configured to control the frequency or rate of the pulses generated by the pulse generator (e.g., 116).

Step 410, which is also performed in response to the onset of patient activity being detected, involves activating the temperature sensor (e.g., 158). Step 408 can be performed by the controller (e.g., 112). In FIG. 4, step 410 is shown after step 408, but these steps can alternatively be performed in reverse order or at the same time, but are not limited thereto.

Step 412 involves determining whether the onset of patient activity, as initially detected (at step 406) based on at least one of one or more outputs of the motion sensor, is confirmed or rejected based on at least one of the one or more outputs of the temperature sensor (e.g., 158).

For example, an output of the temperature sensor, which is indicative of sensed core blood temperature, can be monitored to determine whether the patient's core blood temperature has changed by at least a specified threshold amount within a specified threshold amount of time. Such an output of the temperature sensor can specify the patient's core blood temperature in degrees Celsius (C) or Fahrenheit (F), or can more generally be proportional to the patient's blood temperature, such that increases in the output are indicative of and proportional to increases in the patient's core blood temperature, and decreases in the output are indicative of and proportional to decreases in the patient's blood pressure.

In accordance with certain embodiments, the onset of patient activity can be confirmed in response to detecting a drop in blood temperature by at least a threshold drop amount within a first specified amount of time. Additionally, or alternatively, the onset of patient activity can be confirmed in response to detecting an increase in blood temperature by a threshold increase amount within a second specified amount of time, which can be the same or different than the first specified amount of time. For example, the first specified amount of time can be 5 seconds, and the second specified amount of time can be 10 seconds, or vice versa, which examples are not intended to be limiting. The threshold drop amount can be, e.g., in the range of 0.03 to 0.24 degrees C., and in one embodiment can be 0.06 degrees C., but is not limited thereto. The threshold increase amount can be, e.g., in the range of 0.06 to 0.24 degrees C., and in one embodiment can be 0.12 degrees C., but is not limited thereto. If the initial detection of the onset of patient activity is not confirmed then it is rejected.

If the initial detection of the onset of patient activity is rejected, then flow goes to step 414. Step 414 involves causing the pulse generator (e.g., 116) to reduce the pacing rate from the increased rate back to the base rate. If the initial detection of the onset of patient activity is confirmed, the flow goes to step 416 and the pulse generator is controlled to maintain the increased pacing rate. Alternatively, at step 416, or a further step, the pacing rate can be further increased if the activity is maintained for at least some length of time, and/or if a level of the activity is increased further as detected using the temperature sensor and/or the motion sensor. Steps 412, 414 and/or 416 can be performed by a controller (e.g., 112). Such a controller (e.g., 112) can include one or more processors. Such a controller can additionally, or alternatively, include one or more comparators and/or logic gates that are collectively configured to compare one or more outputs to one or more respective thresholds and trigger responses in the manners summarized with reference to the high-level flow diagram of FIG. 4.

In accordance with still other embodiments, both the motion sensor and the temperature sensor are initially activated, and then whenever an onset of patient activity is detected by either one (or both), the sensor that is providing the better activity metric (e.g., a greater signal-to-noise ratio and/or a greater increase in relative amplitude) becomes the primary sensor while the other sensor is put into a low-power state.

While many of the embodiments of the present technology described above have been described as being for use with LP type IMDs, embodiments of the present technology can also be used with other types of IMDs besides an LP. Accordingly, unless specifically limited to use with an LP, the claims should not be limited to use with LP type IMDs. For example, the embodiments of the present technology can be used with pacemakers, ICDs, and other types of IMDs that are implanted in a subcutaneous pocket, wherein such a pacemaker, ICD or other type of IMD may or may not include leads having electrodes thereon. A motion sensor and/or temperature sensor can be included in the housing of such an alternative type of IMD, or can be included within or otherwise be attached to a lead. Other variations are also possible and within the scope of the embodiments described herein.

In many of the embodiments described above, an IMD (e.g., an LP, pacemaker, ICD, etc.) was described as including both a motion sensor and a temperature sensor, with one of the sensor being used to detect the initial onset of patient activity, and the other sensor being used to confirm or reject the initial detection of the onset of patient activity. Where a patient includes multiple (e.g., two) IMDs that communicate with one another, one of the IMDs can include a motion sensor, and another can include a temperature sensor. In such embodiments, one of the IMDs can use its sensor (e.g., a motion sensor) to detect the initial onset of patient activity, and another IMD can use its sensor (e.g., a temperature sensor) to confirm or reject the initial detection of the onset of patient activity, or vice versa. More generally, many of the embodiments of the present technology described above can be implemented using either a single IMD or multiple IMDs. In other words, an implantable system of the present technology can include one or more IMDs, each of which can include one or more sensors capable of detecting patient activity.

It is to be understood that the subject matter described herein is not limited in its application to the details of construction and the arrangement of components set forth in the description herein or illustrated in the drawings hereof. The subject matter described herein is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Further, it is noted that the term "based on" as used herein, unless stated otherwise, should be interpreted as meaning based at least in part on, meaning there can be one or more additional factors upon which a decision or the like is made. For example, if a decision is based on the results of a comparison, that decision can also be based on one or more other factors in addition to being based on results of the comparison.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the embodiments of the present technology without departing from its scope. While the dimensions, types of materials and coatings described herein are intended to define the parameters of the embodiments of the present technology, they are by no means limiting and are exemplary embodiments. Many other embodiments will be apparent to those of skill in the art upon reviewing the above description. The scope of the embodiments of the present technology should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means—plus-function format and are not intended to be interpreted based on 35 U.S.C. § 112(f), unless and until such claim limitations expressly use the phrase "means for" followed by a statement of function void of further structure.

What is claimed is:

1. A leadless cardiac pacemaker configured to be implanted in a chamber of a patient's heart, comprising:
    a temperature sensor configured to produce one or more outputs indicative of blood temperature when the temperature sensor is activated;
    a motion sensor configured to produced one or more outputs indicative of activity when the motion sensor is activated;
    a pulse generator configured to produce pulses that are used to pace the chamber of the patient's heart within which the leadless cardiac pacemaker is configured to be implanted;
    a controller communicatively coupled to the temperature sensor, the motion sensor, and the pulse generator;
    a battery configured to supply power to the controller and other components of the leadless cardiac pacemaker when they are activated; and
    a housing configured to be attached to tissue of the chamber of the patient's heart within which the leadless cardiac pacemaker is configured to be implanted, wherein the temperature sensor, the motion sensor, the pulse generator, and the controller are disposed in the housing;

the controller configured to
> initially detect an onset of patient activity based on at least one of the one or more outputs of the motion sensor, and in response thereto, cause the pulse generator to increase a pacing rate from a base rate to an increased rate;
> differentiate physical non-cardiac motion from cardiac motion so that the onset of patient activity, as detected based on at least one of the one or more outputs of the motion sensor, is not inadvertently detected due to cardiac motion; and
> selectively activate the temperature sensor and use at least one of the one or more outputs of the temperature sensor to confirm or reject the initial detection of the onset of patient activity, as detected based on the at least one of the one or more outputs of the motion sensor.

2. The leadless cardiac pacemaker of claim 1, wherein the controller is configured to initially detect the onset of patient activity, based on the at least one of the one or more outputs of the motion sensor, in response to detecting an increase in motion by at least a threshold amount of motion for at least a threshold amount of time.

3. The leadless cardiac pacemaker of claim 1, wherein the controller is configured to cause the pulse generator to further increase the pacing rate from the increased rate to a further increased rate in response to the controller detecting continued patient activity based on the at least one of the one or more outputs of the temperature sensor.

4. The leadless cardiac pacemaker of claim 1, further comprising:
> at least two electrodes supported by the housing and used to deliver the pulses, produced by the pulse generator, to the chamber of the patient's heart within which the leadless cardiac pacemaker is configured to be implanted.

5. The leadless cardiac pacemaker of claim 1, wherein the controller is further configured to cause the pulse generator to reduce the pacing rate from the increased rate to the base rate in response to the initial detection of the onset of patient activity being rejected using the temperature sensor.

6. The leadless cardiac pacemaker of claim 1, wherein the controller is configured to ignore the one or more outputs of the motion sensor during periods of cardiac motion to thereby differentiate the physical non-cardiac motion from the cardiac motion.

7. The leadless cardiac pacemaker of claim 6, further comprising:
> at least two electrodes located within, on, or near the housing, and used for sensing cardiac electrical activity; and
> wherein the controller is configured to ignore the one or more outputs of the motion sensor during the periods of cardiac motion by ignoring the one or more outputs of the motion sensor for a duration between a QRS complex and a following T-wave.

8. The leadless cardiac pacemaker of claim 7, wherein:
the controller is configured to ignore the one or more outputs of the motion sensor for the duration between the QRS complex and the following T-wave by blanking the one or more outputs of the motion sensor for the duration between the QRS complex and the following T-wave.

9. The leadless cardiac pacemaker of claim 1, wherein:
a baseline cardiac motion signal is sensed using the motion sensor when it is known that the patient is not moving; and
the controller is configured to subtract the baseline cardiac motion signal from the at least one of the one or more outputs of the motion sensor to thereby differentiate the physical non-cardiac motion from the cardiac motion.

10. The leadless cardiac pacemaker of claim 1, wherein:
the temperature sensor is kept in a low power mode when not selectively activated by the controller to confirm or reject the initial detection of the onset of patient activity, as initially detected based on the at least one of the one or more outputs of the motion sensor.

11. A method for use by a leadless cardiac pacemaker implanted in a chamber of a patient's heart, wherein the leadless cardiac pacemaker includes
> a temperature sensor configured to produce one or more outputs indicative of blood temperature when the temperature sensor is activated;
> a motion sensor configured to produced one or more outputs indicative of activity when the motion sensor is activated;
> a pulse generator configured to produce pulses that are used to pace the chamber of the patient's heart within which the leadless cardiac pacemaker is implanted;
> a controller communicatively coupled to the temperature sensor, the motion sensor, and the pulse generator;
> a battery configured to supply power to the controller and other components of the leadless cardiac pacemaker when they are activated; and
> a housing configured to be attached to tissue of the chamber of the patient's heart within which the leadless cardiac pacemaker is implanted, wherein the temperature sensor, the motion sensor, the pulse generator, and the controller are disposed in the housing;

the method comprising:
> initially detecting an onset of patient activity based on at least one of the one or more outputs of the motion sensor, and in response thereto, causing the pulse generator to increase a pacing rate from a base rate to an increased rate;
> differentiating physical non-cardiac motion from cardiac motion so that the onset of patient activity, as detected based on the at least one of the one or more outputs of the motion sensor, is not inadvertently detected due to cardiac motion; and
> selectively activating the temperature sensor and using at least one of the one or more outputs of the temperature sensor to confirm or reject the initial detection of the onset of patient activity, as detected based on the at least one of the one or more outputs of the motion sensor.

12. The method of claim 11, wherein the initially detecting the onset of patient activity, based on the at least one of the one or more outputs of the motion sensor, occurs in response to detecting an increase in motion by at least a threshold amount of motion for at least a threshold amount of time.

13. The method of claim 11, further comprising causing the pulse generator to maintain the increased pacing rate, or further increase the pacing rate from the increased rate to a further increased rate, in response to detecting continued patient activity based on the at least one of the one or more outputs of the temperature sensor.

14. The method of claim 11, wherein:
the leadless cardiac pacemaker further comprises at least two electrodes supported by the housing and used to deliver the pulses, produced by the pulse generator, to the chamber of the patient's heart within which the leadless cardiac pacemaker is implanted.

15. The method of claim 11, further comprising causing the pulse generator to reduce the pacing rate from the increased rate to the base rate in response to the initial detection of the onset of patient activity being rejected using the temperature sensor.

16. The method of claim 11, wherein the differentiating the physical non-cardiac motion from the cardiac motion includes ignoring the one or more outputs of the motion sensor during periods of the cardiac motion.

17. The method of claim 16, wherein:
the leadless cardiac pacemaker includes at least two electrodes located within, on, or near the housing, and used for sensing cardiac electrical activity; and
the ignoring the one or more outputs of the motion sensor during the periods of the cardiac motion comprises ignoring the one or more outputs of the motion sensor for a duration between a QRS complex and a following T-wave.

18. The method of claim 17, wherein:
the ignoring the one or more outputs of the motion sensor for the duration between the QRS complex and the following T-wave comprises blanking the one or more outputs of the motion sensor for the duration between the QRS complex and the following T-wave.

19. The method of claim 11, wherein:
a baseline cardiac motion signal is sensed using the motion sensor when it is known that the patient is not moving; and
the differentiating the physical non-cardiac motion from the cardiac motion includes subtracting the baseline cardiac motion signal from the at least one of the one or more outputs of the motion sensor to thereby differentiate the physical non-cardiac motion from the cardiac motion.

20. The method of claim 11, further comprising:
maintaining the temperature sensor in a low power mode when not selectively activated to confirm or reject the initial detection of the onset of patient activity, as initially detected based on the at least one of the one or more outputs of the motion sensor.

\* \* \* \* \*